US011660411B2

(12) United States Patent
Wedler et al.

(10) Patent No.: US 11,660,411 B2
(45) Date of Patent: May 30, 2023

(54) RESPIRATORY DEVICE AND METHOD FOR CONTROLLING A RESPIRATORY DEVICE

(71) Applicant: Loewenstein Medical Technology S.A., Luxembourg (LU)

(72) Inventors: Wolfgang Wedler, Hamburg (DE); Bjoern Tiemann, Ahrensberg (DE); Christof Goebel, Hamburg (DE)

(73) Assignee: Loewenstein Medical Technology S.A., Luxembourg (LU)

(*) Notice: Subject to any disclaimer, the term of this patent is extended or adjusted under 35 U.S.C. 154(b) by 1108 days.

(21) Appl. No.: 16/355,969

(22) Filed: Mar. 18, 2019

(65) Prior Publication Data

US 2019/0209793 A1    Jul. 11, 2019

Related U.S. Application Data

(60) Division of application No. 13/960,717, filed on Aug. 6, 2013, now Pat. No. 10,252,013, which is a (Continued)

(30) Foreign Application Priority Data

Feb. 10, 2004  (DE) .................. 102004006396.6

(51) Int. Cl.
*A61M 16/00*  (2006.01)
*A61M 16/06*  (2006.01)
(Continued)

(52) U.S. Cl.
CPC ......... *A61M 16/0051* (2013.01); *A61B 5/087* (2013.01); *A61B 5/4836* (2013.01);
(Continued)

(58) Field of Classification Search
CPC ....... A61M 2016/002; A61M 2016/003–0042; A61M 16/0069; A61M 16/0858; A61M 16/024; A61M 16/06; A61M 2230/40
See application file for complete search history.

(56) References Cited

U.S. PATENT DOCUMENTS 2,567,225 A * 9/1951 McKee .................. A61M 16/00
251/75
3,599,633 A   8/1971 Beasley
(Continued)

FOREIGN PATENT DOCUMENTS

CA    2323455 A1 * 9/1999 ............ A61M 16/00
DE    10014427 A1   10/2001
(Continued)

*Primary Examiner* — Michael J Tsai
(74) *Attorney, Agent, or Firm* — Abel Schillinger, LLP

(57) ABSTRACT

A respiratory device having a respiratory gas source, a control unit and a connecting device for connecting to a respiratory mask. The control unit is connected to a sensor for detecting a measurement parameter. The control unit has a step generator for specifying a stepped modification of the pressure that is generated by the respiratory gas source. The sensor measures a signal that corresponds to the pressure distribution and is coupled to an analyzer that evaluates the temporal distribution of an analysis signal that is dependent on the measuring signal. The step generator increases the pressure by a pressure step in a respiratory cycle that follows the measuring evaluation, if the analyzer determines a deviation of the analysis signal from a limit value after a predeterminable time limit has elapsed following the pressure increase. The deviation must exceed a predeterminable minimum differential in order to trigger a pressure increase.

19 Claims, 5 Drawing Sheets

Related U.S. Application Data continuation of application No. 10/588,979, filed as application No. PCT/DE2004/002678 on Dec. 7, 2004, now abandoned.

(51) Int. Cl.
  *A61M 16/08* (2006.01)
  *A61B 5/087* (2006.01)
  *A61B 5/00* (2006.01)

(52) U.S. Cl.
  CPC .... *A61M 16/0057* (2013.01); *A61M 16/0069* (2014.02); *A61M 16/024* (2017.08); *A61M 16/06* (2013.01); *A61M 16/0858* (2014.02); *A61M 2016/0036* (2013.01)

(56) References Cited

U.S. PATENT DOCUMENTS

| | | | |
|---|---|---|---|
| 3,923,056 A | 12/1975 | Bingmann | |
| 4,592,349 A * | 6/1986 | Bird .................. | B05B 7/0012 417/183 |
| 4,773,411 A * | 9/1988 | Downs ................. | A61M 16/00 128/204.21 |
| 5,345,930 A * | 9/1994 | Cardinal ........... | A61M 16/0006 128/205.24 |
| 5,353,788 A * | 10/1994 | Miles ................. | A61M 16/00 128/204.26 |
| 5,390,666 A * | 2/1995 | Kimm ................. | A61M 16/00 128/204.26 |
| 5,474,062 A * | 12/1995 | DeVires ............ | A61M 16/0051 128/205.24 |
| 5,582,163 A * | 12/1996 | Bonassa ............ | A61M 16/0051 128/204.26 |
| 6,105,575 A * | 8/2000 | Estes ................. | A61M 16/0069 128/204.23 |
| 6,345,619 B1 * | 2/2002 | Finn .................... | A61M 16/024 128/204.26 |
| 6,367,474 B1 | 4/2002 | Berthon-Jones | |
| 6,398,739 B1 | 6/2002 | Sullivan | |
| 6,484,719 B1 | 11/2002 | Berthon-Jones | |
| 6,564,798 B1 | 5/2003 | Jalde | |
| 6,588,422 B1 | 7/2003 | Berthon-Jones | |
| 6,752,151 B2 | 6/2004 | Hill | |
| 6,793,629 B2 | 9/2004 | Rapoport | |
| 6,820,618 B2 | 11/2004 | Banner | |
| 7,305,987 B2 | 12/2007 | Scholler | |
| 2007/0221224 A1 * | 9/2007 | Pittman ............... | A61M 16/204 128/203.14 |
| 2008/0041382 A1 * | 2/2008 | Matthews .......... | A61M 16/204 128/201.24 |
| 2008/0283061 A1 * | 11/2008 | Tiedje ................. | A61M 16/024 128/204.23 |
| 2008/0295839 A1 * | 12/2008 | Habashi ............ | A61M 16/0003 128/204.22 |
| 2009/0078255 A1 * | 3/2009 | Bowman ............ | A61M 16/204 128/204.23 |
| 2010/0108066 A1 * | 5/2010 | Martin ................ | A61M 16/204 128/204.23 |
| 2015/0107592 A1 * | 4/2015 | Allum .................. | A61M 16/20 702/50 |

FOREIGN PATENT DOCUMENTS

| | | | | |
|---|---|---|---|---|
| DE | 10212497 A1 | 10/2003 | | |
| DE | 10212783 A1 | 11/2003 | | |
| DE | 10237973 A1 | 3/2004 | | |
| DE | 20315975 A1 | 5/2004 | | |
| DE | 102008060799 B3 * | 4/2010 | ............ | A61M 16/00 |
| JP | 2002528186 A * | 9/2002 | ............ | A61M 16/00 |
| JP | 3737698 B2 * | 1/2006 | ............ | A61M 16/00 |
| WO | 200074755 A1 | 12/2000 | | |
| WO | WO-0119440 A1 * | 3/2001 | ............ | A61M 16/00 |
| WO | WO-03075989 A2 * | 9/2003 | ........ | A61M 16/0057 |
| WO | WO-2015120521 A1 * | 8/2015 | ........... | A61B 5/0816 |
| WO | WO-2015131219 A1 * | 9/2015 | ........ | A61M 16/0051 |

\* cited by examiner

RESPIRATORY DEVICE AND METHOD FOR CONTROLLING A RESPIRATORY DEVICE

CROSS-REFERENCE TO RELATED APPLICATIONS

The present application is a Divisional Application of U.S. patent application Ser. No. 13/960,717, filed Aug. 6, 2013, which is a Continuation Application of U.S. patent application Ser. No. 10/588,979, filed May 21, 2010, which is a 371 of International Application PCT/DE04/02678, filed Dec. 7, 2004, which claims priority under 35 U.S.C. 119 of German patent application No. 10 2004 006 396.6, filed Feb. 10, 2004. The priorities of these applications are hereby claimed and the entire disclosures of these applications are incorporated by reference herein.

BACKGROUND OF THE INVENTION

The invention concerns a ventilation device with a breathing gas source, a control unit, and a connecting device for connecting the device to a ventilation mask, where the control unit is connected to at least one sensor for detecting a test parameter.

In addition, the invention concerns a method for controlling a ventilator, in which a breathing gas source is controlled by a control unit as a function of at least one test parameter.

A device of this type and the method for controlling the ventilator can be used, for example, in connection with so-called bi-level ventilation. The ventilator produces inspiratory pressure and an expiratory pressure. Basically, in is necessary to distinguish among controlled ventilation, assisted ventilation, and mixed forms of ventilation.

In controlled ventilation, the respiratory parameters during inspiration are completely determined by the ventilator. There are basically two forms of controlled ventilation, namely, volume-controlled and pressure-controlled ventilation. In volume-controlled ventilation, a well-defined tidal volume is delivered breath by breath; the pressure can vary between the respiratory strokes as a function of resistance. The basis for the switch to the expiratory phase is the attainment of a predetermined target volume or inspiration time. In pressure-controlled ventilation, the therapeutic pressure is held constant. The resulting volume can vary as a function of mechanical respiratory parameters. The switch to the expiratory phase is controlled as a function of time.

In volume-controlled ventilation, the administration of a sufficient, well-defined gas volume per respiratory stroke is the main consideration. Pressure-controlled ventilation has the advantage that when the parameters are suitably adjusted, there are no impermissible pressure peaks to damage lung tissue. Of course, the administered tidal volume is strongly dependent on the cooperation of the patient with respiration and on the mechanical respiratory variables of resistance and lung compliance. On the other hand, volume-control led ventilation basically makes sense primarily in the case of invasive ventilation, since leakage occurs during mask ventilation, and such leakage makes it impossible to measure the actual control parameter accurately, even when the leakage that occurs is included in the calculations.

In pressure and volume-controlled ventilation, the advantages of volume-controlled ventilation are combined with those of pressure-controlled ventilation. The administered ventilation volume depends on the mechanical properties of the lung and on the ventilation pressure. If the volume falls below a preset value, the inspiratory pressure is increased in small increments during the following respiratory strokes until the target volume is reached.

In assisted ventilation, the patient himself can determine the times at which he inspires and expires. The ventilation strokes of the apparatus are thus synchronized with the inspiratory and expiratory effort of the patient. The ventilation strokes of the apparatus are volume-controlled or pressure-controlled. In assisted, pressure-controlled ventilation the ventilator switches between an inspiratory and an expiratory pressure level synchronously with the respiratory effort of the patient.

Assisted ventilation in so-called S mode allows free switching between inspiratory and expiratory pressure (IPAP, EPAP), depending on the breaths initiated by the patient (triggered by spontaneous respiration).

In assisted ventilation in so-called ST mode, the ST mode describes a mixed form of support of spontaneous respiration (S mode) and mandatory ventilation. A background respiratory rate is determined, by which the minimum gap between respiratory intervals defined. It is possible for the patient to trigger an inspiration within these intervals (from an expiratory phase), i.e., to switch into IPAP by respiratory effort. If the patient fails to trigger an inspiration before the maximum allowed gap is reached, as defined by the background respiratory rate, the ventilator triggers the switch to the inspiratory pressure level to provoke a breath of the patient. This mode also allows mandatory respiration, during which the patient can demand additional breaths.

In another ventilation method, the patient triggers the switch to inspiratory pressure by his respiratory effort. However, he no longer has any freedom with respect to expiration. After a determined inspiratory time, an automatic switch to the expiratory pressure level occurs.

SUMMARY OF THE INVENTION

The objective of the present invention is to design a device of the aforementioned type in such a way that during the inspiration phases, the ventilator generates a pressure in such a way that the ventilator performs the greatest possible portion of the respiratory work.

In accordance with the invention, the solution of this problem is characterized in that
 the control unit has a step generator for predetermining an at least temporary, essentially stepped change in the inspiratory pressure produced by the breathing gas source; in that
 the sensor is designed to measure a signal corresponding to the change in pressure and is connected to an analyzer, which evaluates the change over time in an analysis signal dependent. on the measuring signal; and in that
 the step generator increases the pressure by a pressure step during a ventilation cycle following that in which the measured value was evaluated if, after a predetermined time limit has elapsed following the pressure increase, the analyzer determines that the analysis signal deviates from a limit value by more than a predetermined minimum difference.

A further objective of the present invention is to improve a method of the aforementioned type in a way that supports optimum apparatus control.

In accordance with the invention, the solution of this problem is characterized in that the control unit produces an at least temporary, essentially stepped change in the pressure generated by the breathing gas source; in that the sensor detects a measuring signal corresponding to the change in pressure; in that the change over time in an analysis signal dependent on the measuring signal is evaluated; and in that the inspiratory pressure is increased in a subsequent ventilation cycle if the analysis signal deviates from a limit value by a predetermined minimum difference at a minimum of one predetermined time.

The stepped change in the inspiratory pressure and the corresponding evaluation of the analysis signal make it possible, during the performance of the ventilation, to control the apparatus in such a way that precisely the desired relief of the patient from respiratory work is achieved. This ensures, first, that the relief from respiratory work is not too small and, second, that the ventilator is prevented from generating unnecessarily high pressures.

The invention can basically be realized by two different variants of the method. In accordance with a first variant of the method, the ventilation volume is incrementally increased between one breath and the next, starting from an initial state. This also includes the idea of initially generating the same inspiratory pressure over the course of several successive breaths and then, depending on an evaluation of the analysis signal, i.e., if the triggering condition for a pressure increase is detected, of providing a higher pressure for one or again several successive ventilation cycles.

In the first variant of the method, the use of a measuring instrument to detect a possible decrease in a maximum value of the ventilation volume after a previous pressure increase makes it possible to determine whether the patient's spontaneous activity is contributing to the respiratory volume. After the pressure has been increased, the patient at first typically continues his own respiratory work at the same level, so that the respiratory volume produced by the apparatus and the respiratory volume produced by the patient are additive. After a certain reaction time, the patient then automatically reduces his spontaneous activity, so that a decrease in the ventilation volume can be detected by measurement. The decrease can occur, for example, incrementally or successively.

After a pressure increase, the ventilation pressure is typically maintained at a constant level for several ventilation cycles, and the time interval after which a possible volume reduction is evaluated automatically extends over several ventilation cycles of inspiratory and expiratory phases. If the patient has completely stopped his own breathing activity, no decrease in the ventilation volume relative to the response volume that develops will be detected after a pressure increase, since there is no activity of the patient's own which can be reduced, and ventilation will be completely determined by the ventilator. The maximum value of the ventilation volume during the first ventilation cycle following the pressure increase can used here as the limit value with which the maximum value of the ventilation volume is compared during the ventilation cycles following the pressure increase.

In accordance with a second variant of the method of the invention, ventilation is carried out during the vast majority of breaths with a standard ventilation pressure curve, in which the slope of the pressure as a function of time decreases over the course of breaths during the inspiration phase, after which, at the end of the inspiration phase, there is a relative steep drop to the expiration pressure, which is essentially constant during the expiration phase. Pressure curves which the pressure is increased in stepwise fashion for one or more breaths and have a more or less square-wave form are then incorporated into this sequence of standard ventilation pressure curves.

If a detected flow curve approximately follows the square-wave pressure curve over at least most of the inspiration phase, then active patient breathing is occurring. If, after an increase of the flow curve following the stepped increase in pressure, there is a decline in the flow volume while the applied pressure continues at a constant level, this is a sign of a passive lung of the patient. When a flow curve of this type is detected for the first time after a stepwise pressure increase, the sought-for pressure level for relieving the patient from respiratory work has just been found.

The use of sensors of simple design is facilitated by designing the sensor as a flow sensor.

To determine a signal for the ventilation volume without direct volume measurement, it is proposed that an integrator be connected downstream from the sensor.

The automatic control can be optimized by designing the control unit to lower the pressure by a pressure step via the step generator the first time a decrease in the ventilation volume following a pressure increase is not detected. Expanded functionality is achieved by connecting the control unit to a setpoint memory for the setpoints of the ventilation volume.

In a typical control sequence, the control unit is connected to a square-wave generator for defining the pressure curves during the inspiration and expiration phases.

To generate individually adapted pressure curves, it is also proposed that the control unit be connected to a curve generator for defining the pressure curves during the inspiration and expiration phases.

Standardized signal processing is facilitated if the analyzer evaluates the pressure difference between the inspiration phases and the expiration phases.

According to another variant of automatic pressure control, the step generator lowers the expiratory pressure to increase the pressure difference.

It is easier to carry out ventilation with a well-defined volume curve if the control unit uses setpoints to adjust the ventilation volume.

In an advantageous variant of the automatic control, the control unit calls for a pressure decrease only when an actual value of the ventilation volume exceeds the given setpoint.

It is also proposed that, in a first step, the control unit increase the pressure until the ventilation volume reaches the predetermined setpoint, and that the pressure then be increased again.

Another automatic control variant is defined by the fact that an at least approximately square-wave form pressure increase is selected for at least a single breath.

In particular, it is possible for the flow curve following the stepped pressure increase to be analyzed for the presence of an increase to a maximum and a subsequent deceleration.

BRIEF DESCRIPTION OF THE DRAWING

The drawings show schematic illustrations of specific embodiments of the invention.

DETAILED DESCRIPTION OF THE INVENTION

Figure 1:
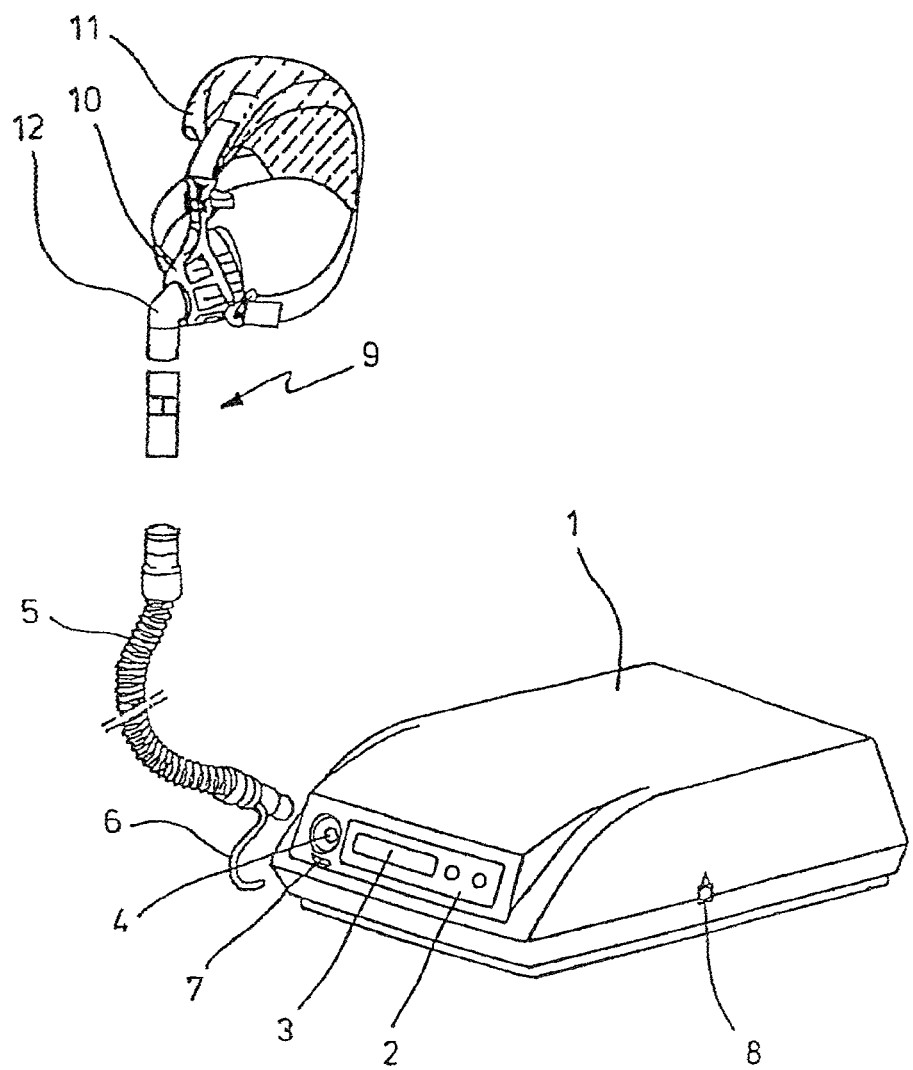
FIG. 1 shows a perspective view of a ventilator with a connecting hose running to a ventilation mask.

FIG. 1 shows the basic design of a ventilation device. In the area of the unit housing (1), which has a control panel (2) and a display (3), a breathing gas pump installed in an internal space in the unit. A connecting hose (5) is attached to a socket (4). An additional pressure-measuring hose (6), which can be connected to the unit housing CO by a pressure input connection (7), can run along the connecting hose (5). To allow data transmission, the unit housing (1) has an interface (8).

An expiratory device (9) is installed in an expanded area of the connecting hose (5) at the end facing away from the unit housing (1). An expiratory valve can also be used.

FIG. 1 also shows a ventilation mask (10), which is designed as a nasal mask. In another embodiment, it is also possible to use a full-face mask. The mask can be held in place on the patient's head by a head fastening device (11). A hose connector (12) is provided in the expanded region of the ventilation mask (10) on the side facing the connecting hose (5).

Figure 2:
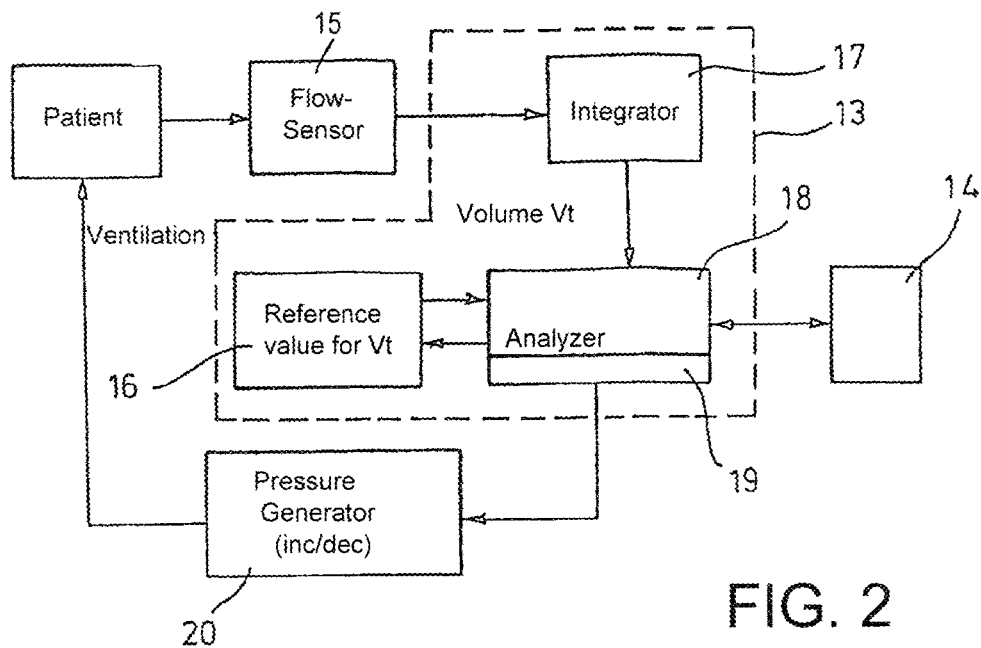
FIG. 2 is a schematic diagram of the essential functional components.

FIG. 2 shows the basic design of the automatic control components of the ventilation device. A control unit (13) is provided with an input module (14) for data input. The desired ventilation values can be entered by a physician, for example, via the input module (14). The control unit (13) is connected to a sensor (15), which detects at least one ventilation. parameter of a patient.

In the illustrated embodiment, the sensor (15) is designed as a flow sensor, which sends its measuring signal to an integrator (17) to determine a volume value. The integrator (17) is connected to an analyzer (18) for evaluating the volume curve. The analyzer (18) is also supplied with a volume reference value stored in the setpoint memory (16). In addition, the analyzer (18) is connected to a step generator (19), which defines a given nominal pressure for the breathing gas source.

Figure 3:
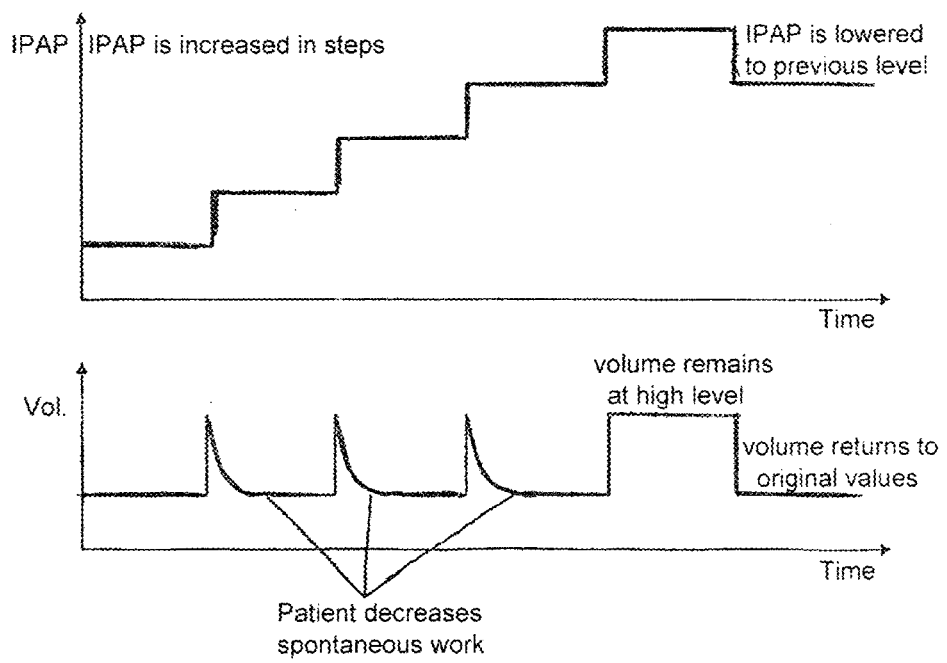
FIG. 3 shows a graph of pressure as a function of time and a graph of volume as a function of time with envelopes for the actual curves.

The automatic control sequence is further explained by the graphs in FIG. 3. The illustrated curves are each envelopes for the actual pressure and volume curves obtained as a function of the given ventilation rate. To begin with, it is apparent that, when the first pressure increases are effected, there are also sudden increases in the ventilation volume. After each increase, the ventilation volume decreases again. This system behavior is characteristic of a patient with some remaining spontaneous activity. After the fourth pressure increase shown in the drawing, however, the ventilation volume remains at the high level that was reached. This is the result of the cessation of the spontaneous activity of the patient that has already occurred at this point. To help optimize the operation of the apparatus, the ventilation pressure produced can thus be dropped back a step.

Figure 4:
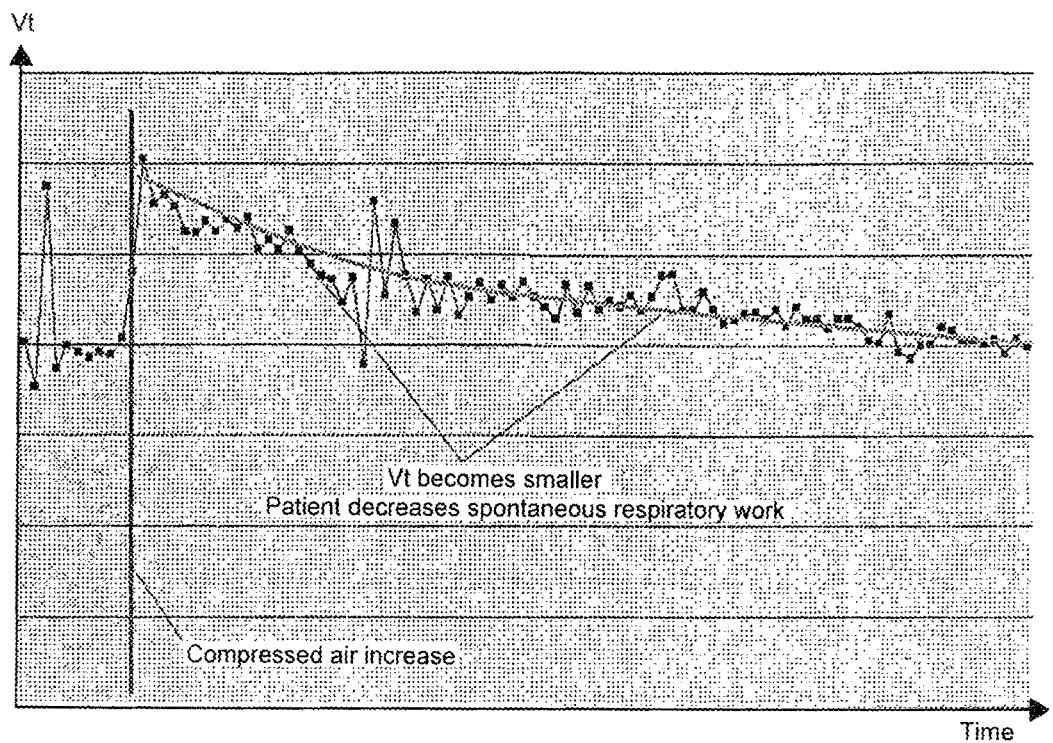
FIG. 4 shows a graph of volume as a function of time after a pressure increase with actual volume values measured from breath to breath in the presence of spontaneous patient breathing activity.

FIG. 4 shows the measured ventilation volume from breath to breath for a patient who is still showing spontaneous activity. The graph shows that after an initial sudden increase in the ventilation volume following a pressure increase, the ventilation volume returns approximately to its initial value. The values actually measured are scattered within a tolerance range around a decreasing curve similar to an exponential function.

Figure 5:
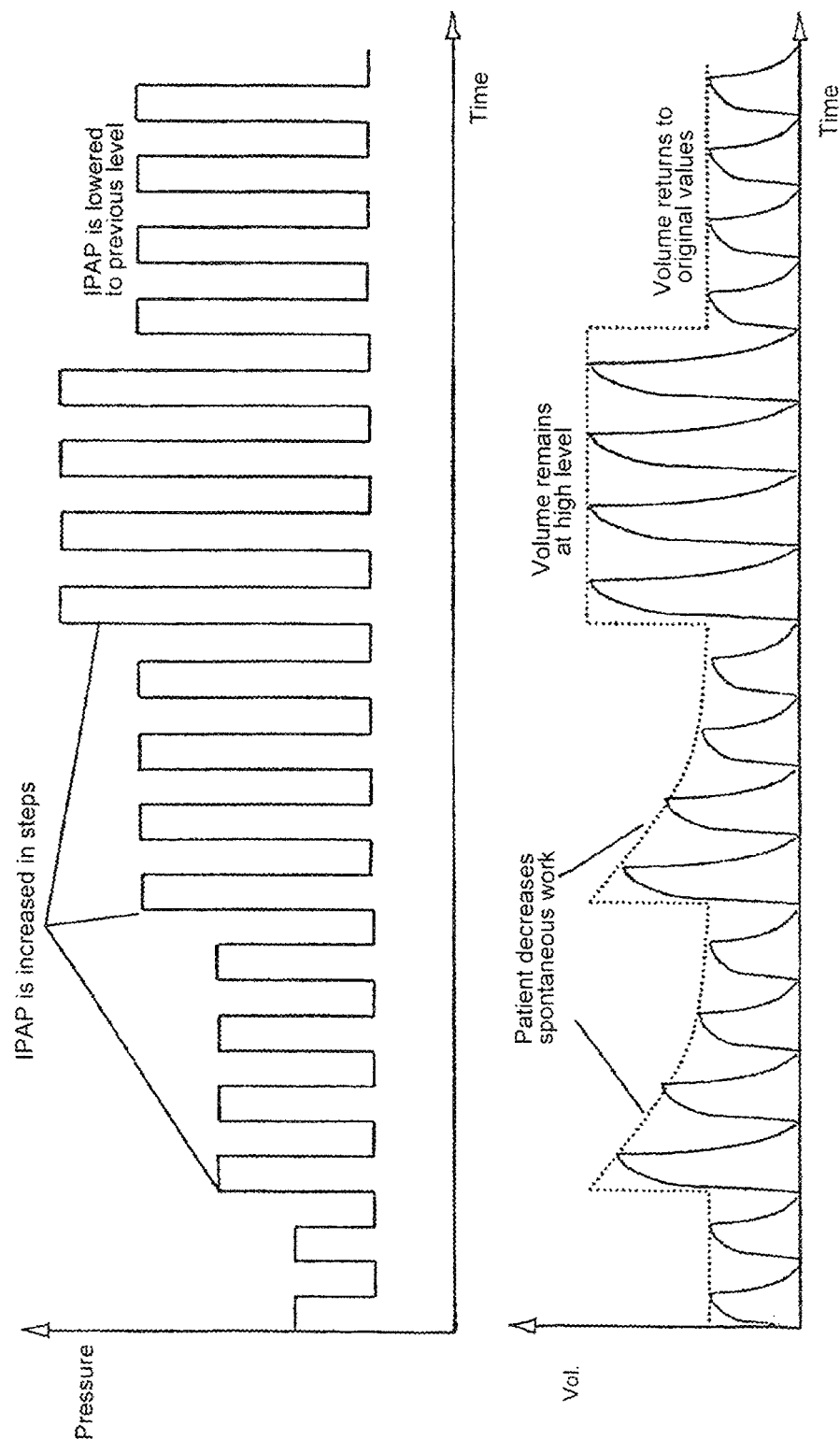
FIG. 5 shows graphs in greater detail than FIG. 3 with a series of several successive ventilation cycles at the same inspiratory pressure.

FIG. 5 shows the pressure curves represented as envelopes in FIG. 3 in greater detail. The graphs show that the same inspiratory pressures are specified several times in a row. When spontaneous patient activity is still present, the peak values of the analysis signal decrease from breath to breath in the corresponding volume curves. When the pressure reaches a level high enough that all of the patient's work is being done for him, the analysis signal remains at approximately the same maximum value from breath to breath.

Figure 6:
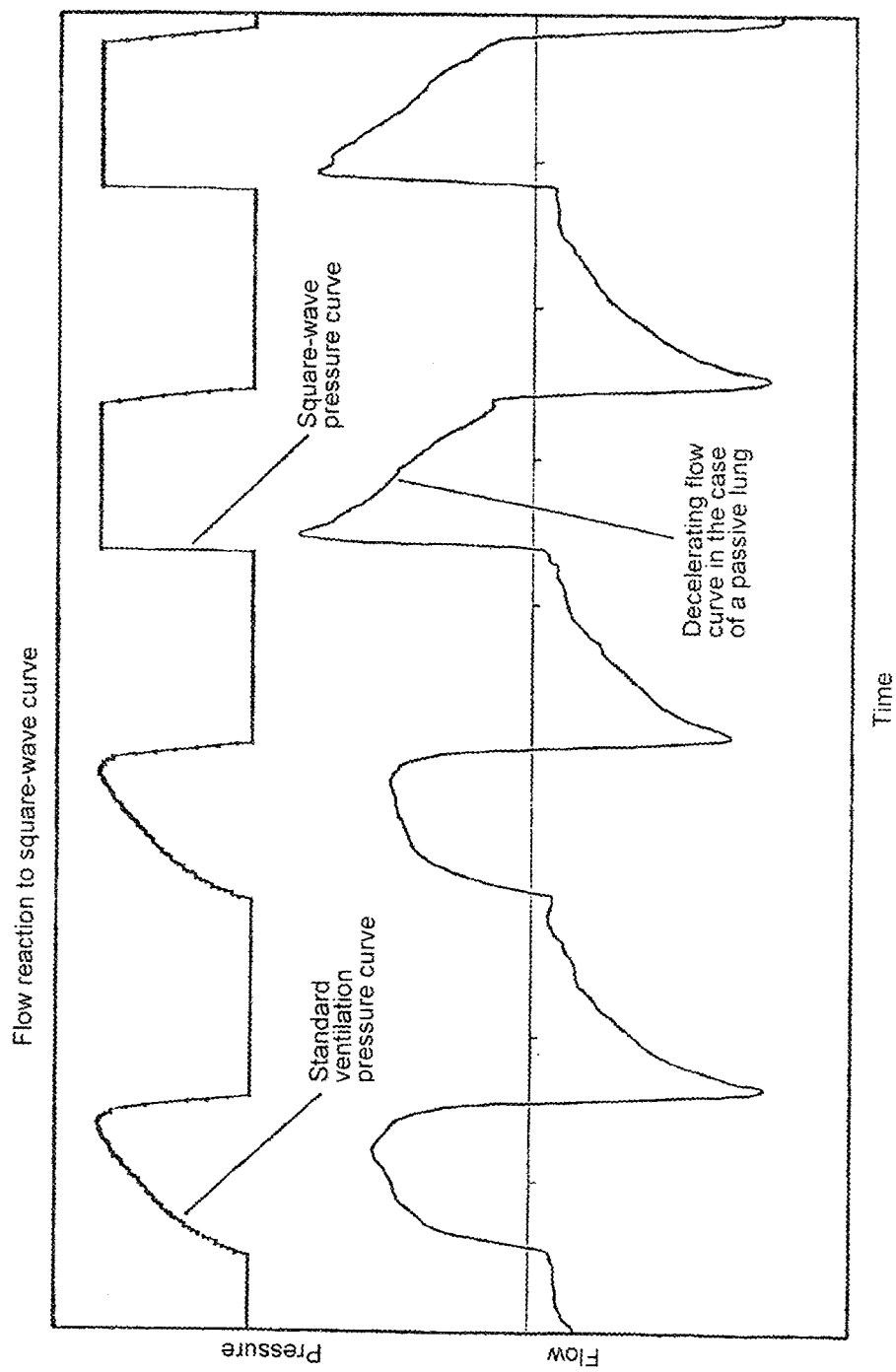
FIG. 6 shows curves of pressure and flow as a function of time with preselection of a rectangular pressure increase for an individual breath.

Alternatively or additionally to the measurement of a test parameter corresponding to the volume curve, it is also possible, when ventilation is being carried out with a pressure curve that deviates from the square-wave form, to specify an at least approximately square pressure increase for an individual breath and to measure the flow that develops. This possibility is shown in FIG. 6. In the absence of spontaneous respiratory activity of the patient, the flow will increase rapidly to a maximum and then decelerate as the result of a passive lung. If this flow behavior is not present, the analyzer (18) will conclude that the patient is actively breathing.

In particular, when there is definite deviation from this flow behavior, it can be concluded that there is a high degree of spontaneous activity of the patient.

What is claimed is:

1. A ventilation device, wherein the ventilation device comprises a breathing gas source, a control unit, and a connecting device for connecting the device to a ventilation mask, the control unit being connected to at least one sensor for detecting a test parameter and comprising a step generator for determining an at least temporary, essentially stepped change in an inspiratory pressure produced by the breathing gas source; wherein the at least one sensor is designed to measure a signal corresponding to the change in pressure and is connected to an analyzer, which evaluates a change over time in an analysis signal dependent on the measured signal; wherein the step generator increases the pressure by a pressure step during a ventilation cycle following that in which a measured value was evaluated if, after a predetermined time limit has elapsed following the pressure increase, the analyzer determines that the analyzed signal deviates from a limit value by more than a predetermined minimum difference, the analyzer being designed to evaluate the changes in a ventilation volume as the analysis signal, wherein a maximum value of the ventilation volume during a first ventilation cycle following the pressure increase is used as the limit value with which the maximum value of the ventilation volume is compared during ventilation cycles following the pressure increase.

2. A ventilation device, wherein the ventilation device comprises a breathing gas source, a control unit, and a connecting device for connecting the device to a ventilation mask, the control unit being connected to at least one sensor for detecting a test parameter, wherein the control unit comprises a step generator for determining an at least temporary, essentially stepped change in an inspiratory pressure produced by the breathing gas source; wherein the sensor is designed to measure a signal corresponding to the change in pressure and is connected to an analyzer which evaluates the change over time in an analysis signal dependent on the measured signal; wherein the step generator increases the pressure by a pressure step during a ventilation cycle following that in which the measured value was evaluated if, after a predetermined time limit has elapsed following the pressure increase, the analyzer determines that the analyzed signal deviates from a limit value by more than a predetermined minimum difference, wherein the analyzer is designed to evaluate the changes in a ventilation volume as the analysis signal, wherein a decrease in the ventilation volume relative to the ventilation volume observed immediately after a pressure increase is detected, and the control unit increases the pressure precisely when the decrease in the ventilation volume exceeds a predetermined minimum difference after a predetermined time following the pressure increase has elapsed.

3. A method for controlling a ventilator comprising a breathing gas source and a control unit connected to at least one sensor for detecting at least one test parameter, wherein the method comprises controlling the breathing gas source by the control unit as a function of the at least one test parameter, the control unit producing an at least temporary, essentially stepped change in pressure generated by the breathing gas source and the sensor detecting a measuring signal corresponding to the change in pressure; evaluating a change over time in an analysis signal dependent on the measuring signal, and increasing an inspiratory pressure in a subsequent ventilation cycle whenever the analysis signal deviates from a limit value by a predetermined minimum difference at a minimum of one predetermined time, and detecting a decrease in a ventilation volume relative to a ventilation volume observed immediately after a pressure increase the control unit increasing the pressure precisely when a decrease in the ventilation volume exceeds a predetermined minimum difference after a predetermined time following the pressure increase has elapsed.

4. The method of claim 3, wherein, following an at least approximate step-like pressure increase, the pressure curve realized during the preceding breath is maintained if a decreasing flow at essentially constant pressure is detected after a predetermined time interval following the step-like pressure increase.

5. The method of claim 3, wherein the sensor carries out a flow measurement.

6. The method according to claim 3, wherein a volume signal is produced by integration of a flow signal.

7. The method of claim 3, wherein the pressure is lowered by a pressure step the first time a decrease in the ventilation volume following a pressure increase is not detected.

8. The method of claim 3, wherein the control unit considers a target value for the ventilation volume.

9. The method of claim 3, wherein the ventilation pressure is controlled according to a course of a square-wave signal.

10. The method of claim 3, wherein the ventilation pressure is varied by the control unit according to a predetermined pressure curve.

11. The method of claim 3, wherein a pressure difference between inspiratory and expiratory pressure is determined.

12. The method of claim 11, wherein the pressure difference is increased by lowering the expiratory pressure.

13. The method of claim 3, wherein a pressure is changed from ventilation cycle to ventilation cycle.

14. The method of claim 3, wherein the pressure is held constant for at least two successive inspiration phases.

15. The method of claim 3, wherein the pressure is held constant for at least two successive expiration phases.

16. The method of claim 3, wherein the control unit decreases the pressure only when an actual value of the ventilation volume exceeds a predetermined setpoint.

17. The method of claim 3, wherein, in a first step, the control unit increases the pressure until the ventilation volume reaches a predetermined setpoint, and an additional pressure increase is then carried out.

18. The method of claim 3, wherein an at least approximate square-wave form pressure increase is selected for at least a single breath.

19. The method of claim 18, wherein the flow curve following the stepped pressure increase is analyzed for the presence of an increase to a maximum and a subsequent decelerating curve.

* * * * *